United States Patent
Wagner et al.

(10) Patent No.: US 8,403,840 B2
(45) Date of Patent: Mar. 26, 2013

(54) MEDICAL INSTRUMENT FOR CREATING AN ACCESS FOR A MINIMALLY INVASIVE INTERVENTION

(75) Inventors: Sebastian Wagner, Bretten (DE); Felix Teufel, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 120 days.

(21) Appl. No.: 12/722,709

(22) Filed: Mar. 12, 2010

(65) Prior Publication Data

US 2010/0234689 A1 Sep. 16, 2010

(30) Foreign Application Priority Data

Mar. 13, 2009 (DE) .......... 10 2009 014 525

(51) Int. Cl.
*A61B 1/32* (2006.01)

(52) U.S. Cl. ........ 600/210; 600/201; 600/208; 600/219; 600/220; 600/225

(58) Field of Classification Search ........... 600/201–246
See application file for complete search history.

(56) References Cited

U.S. PATENT DOCUMENTS

| 3,717,151 | A | 2/1973 | Collett |
| 4,432,351 | A | 2/1984 | Hoary |
| 5,580,344 | A | 12/1996 | Hasson |
| 2004/0002629 | A1 | 1/2004 | Branch et al. |
| 2004/0093001 | A1 | 5/2004 | Hamada |
| 2005/0273132 | A1 | 12/2005 | Shluzas et al. |
| 2006/0235279 | A1 | 10/2006 | Hawkes et al. |
| 2007/0027364 | A1 | 2/2007 | Schwer |
| 2007/0219416 | A1 | 9/2007 | Perez-Cruet et al. |
| 2008/0234550 | A1 | 9/2008 | Hawkes et al. |
| 2008/0249371 | A1* | 10/2008 | Beckman et al. ............. 600/204 |
| 2008/0255519 | A1 | 10/2008 | Piskun et al. |
| 2008/0300467 | A1* | 12/2008 | Schaefer ....................... 600/208 |

FOREIGN PATENT DOCUMENTS

| DE | 2801696 A1 | 7/1979 |
| EP | 0043218 A1 | 1/1982 |

OTHER PUBLICATIONS

European Search Report; Application No. EP 10 15 6161; Jun. 30, 2010; 7 pages.

* cited by examiner

*Primary Examiner* — Eduardo C Robert
*Assistant Examiner* — Nicholas Plionis
(74) *Attorney, Agent, or Firm* — St. Onge Steward Johnston & Reens LLC (57) ABSTRACT

A medical instrument serves for creating an access for a minimally invasive intervention and has a body having a longitudinal axis. The body is assembled of at least two parts, each of said parts having edges extending along a direction of said axis. Each of said parts having edges extending along a direction of said axis. Each part has a distal section merging into a proximal section standing outwardly from said longitudinal axis. In a first position, the distal end section of the parts are joined along said edges to form a distal body with the proximal section standing away. In a second position, the proximal sections of said parts are joined along said edges to form a hollow proximal body with said distal end section spreaded outwardly. The edges are provided with interacting features which are designed to block a lateral sliding of said joined parts transversely to said edges.

14 Claims, 11 Drawing Sheets

MEDICAL INSTRUMENT FOR CREATING AN ACCESS FOR A MINIMALLY INVASIVE INTERVENTION

BACKGROUND OF THE INVENTION

The invention relates to a medical instrument for creating an access for a minimally invasive intervention, which instrument has a body.

The body is mostly in the form of a cylindrical sleeve which is driven into the human body via an incision in the skin in order to gain access to a cavity in the interior of the human body.

In laparoscopy, the inner cavity is the abdominal cavity of the body, while in arthroscopy it is, for example, the interior of a joint.

Particularly in laparoscopy, a procedure in which minimally invasive interventions have been widely employed, this access is made via trocars. A trocar is composed of a trocar sleeve, which has a tube measuring approximately 10 cm in length with a housing arranged at the proximal end thereof. The housing in most cases accommodates valves, in order to seal the housing off in relation to lateral connection pieces via which it is possible to introduce, for example, gases for inflating the abdominal cavity or liquids for irrigation. At the proximal end, the trocar housing is provided with a seal that in most cases has a central opening through which, after the trocar sleeve has been fitted, instruments can be pushed into the body, for example endoscopes for visual monitoring, or other surgical instruments.

To put the trocar in place, a trocar mandrel is pushed into the trocar sleeve from the proximal direction, which trocar mandrel is designed such that its sharp tip, in most cases in the shape of a triangle, protrudes past the distal end of the trocar sleeve. A small incision measuring approximately 1 cm in length is made in the skin, the trocar, or the tip of the trocar mandrel protruding from the distal end of the trocar sleeve, is placed on the incision, and the assembly is then pressed through the abdominal wall. Thereafter, the trocar mandrel is withdrawn, and the trocar sleeve is then free to allow a minimally invasive intervention to be performed through it.

In laparoscopy, the trocar sleeve has to be pushed through the abdominal wall which, in humans of normal build, is a few centimeters thick. Several hoses are often connected to the proximal end of the trocar sleeve, and some instruments, for example surgical forceps, protrude very far past the proximal end of the trocar sleeve.

As a result, considerable tilting moments act on the trocar sleeve fitted in the body, thus posing the risk of the trocar tilting laterally from its original orientation.

Since the connected equipment also exerts a force in the direction of gravity in the case of vertical trocars, it may happen that the trocar sleeve moves axially in an undesired manner. A movement in the distal direction can be compensated by the operator to some extent by pulling on the trocar. However, if the trocar is pulled too far in the proximal direction, for example because an instrument to be withdrawn through the trocar sleeve has caught on the distal end of the trocar sleeve, there is a danger of the entire trocar slipping out of the body.

This tilting moment has an even more pronounced effect when operations are being performed in which the trocar is introduced not vertically, but in an oblique or even a horizontal direction.

Attempts were therefore made to hold access instruments of this kind more securely or more effectively on the body.

U.S. Pat. No. 3,717,151 discloses an access cannula in the form of a trocar having, at the distal end, expandable fingers that are oriented in an axial direction for insertion into the body and, after the abdominal wall has been penetrated, can be spread out laterally by an expansion mechanism. Before the sleeve is withdrawn, the expanded fingers then have to be retracted again to allow the cannula to be withdrawn again from the body.

This structure requires a complicated mechanism for controlling the expandable fingers.

US 2008/0234550 A1 describes a minimally invasive access port in which the sleeve, which is pushed into the body, has laterally pivotable plates which, for insertion purposes, can be pivoted in to form a slender body and can then be spread open by an expansion mechanism when in the body.

A disadvantage of these devices is that a complicated mechanism has to be present for expanding and retracting the expandable elements, and this requires a complex structure.

This structure includes numerous corners or niches in which bacteria are able to adhere, such that these devices can be cleaned only with great difficulty, or they have to be dismantled prior to each cleaning procedure.

It should be noted that, in an operation performed in the abdominal cavity for example, four, five or six trocars are inserted in order to allow the various manipulations to be carried out, and, after an intervention has been performed, the trocars have to be made available as quickly as possible for a further intervention.

The object of the present invention is therefore to create an access instrument that has a simple structure and is easy to handle and that can be anchored reliably.

SUMMARY OF THE INVENTION

This object is achieved by a medical instrument for creating an access for a minimally invasive intervention, comprising a body, having a longitudinal central axis, said body being assembled of at least two parts, each of said parts having edges extending along a direction of said axis, and said parts being assembled via said edges, each of said parts having a distal section merging into a proximal section standing outwardly from said longitudinal central axis when said distal sections extend in said axis, wherein in a first position said distal end sections of said parts are joined along said edges to form a distal body with said proximal sections standing outwardly, and in a second position, said proximal sections of said parts are joined along said edges to form a hollow proximal body with said distal sections standing outwardly, wherein a change-over from said first position to said second position, and vice versa, can be brought by pivoting said parts, and wherein said edges being provided with interacting features which are designed to block a lateral sliding of said joined parts transversely to said edges.

To insert the medical instrument into the human body, the individual parts are initially assembled or combined such that they are joined to form a distal body. This body represents an approximately rod-shaped body.

In this state, the instrument can now be pushed through an incision into the body, the depth of insertion being limited by the fact that the proximal sections stand out to the sides in this state of insertion. In this position, the joined distal sections function as a kind of trocar sleeve.

The distal sections of the parts can be inserted individually into the body followed by assembling it within the body.

Seen along the longitudinal central axis, the structure, which corresponds to a trocar sleeve, is composed of at least two parts, of which the at least two proximal sections stand out to the sides like the top of a "Y". The insertion into the body can in this case be carried out conventionally with the aid of a trocar mandrel or a special driving-in tool.

Once placed, the at least two proximal sections standing out to the sides are moved towards each other towards the longitudinal central axis until they form a proximal hollow body, which corresponds as it were to the trocar housing.

During this pivoting movement, the distal sections already inserted into the body are pivoted or spreaded radially outwards, seen from the central longitudinal axis, and thus form a block against the proximal hollow body being pulled away from the skin, i.e. for example the abdominal wall. Depending on the design, the pivoting movement can proceed until the outer face of the pivoted section bears on the inner face of the abdominal wall. In this second position, the distal sections function as a block against withdrawal. The spreaded distal sections allow to pass shaft-like instrument obliquely through the proximal hollow body or to pass several shaft-like instruments.

The provision of interacting features which block a lateral sliding of the joined parts transversely to the edges has the considerable advantages. If one has, for example, assembled two distal sections to a distal body, a lateral slipping or displacing of the joined parts transversely to the edges is avoided.

This facilitates in particular the assembly and the handling of the instrument in the first position that is to say the position in which the distal sections are joined together, when, for example, pushed through an incision in the abdominal wall. This avoids a situation in which, for example, as the joined parts being pushed into the body, adjoined sections are displaced in the lateral direction and come loose from each other. The interacting features support the pivoting movement along the edges during pivoting the parts when bringing them from their first position to their second position or vice versa. This pivoting movement has to be done against the resistance of the skin area through which the distal sections have been passed. In many cases the proximal section enlarges in the curved transition area between the distal section and the proximal section. Therefore, there is a risk that the counter-pressure exerted by the skin tends to release the joined parts which can now be avoided by the interacting features at the edges.

The proximal sections now joined together to the proximal hollow body, form, on one side, a channel passing through the abdominal walls, that is to say the so-called trocar sleeve. On the other side, proximally outside the abdominal wall, this joined proximal section forms the so-called trocar housing. Due to the interacting features, the proximal parts are lying closely one to another, with the result that the connection along this joining line can be made tight.

The pivoting from the first position to the second position can be assisted by a tool which is placed on the proximal sections still extending to the sides, or it can also be done manually, for example by a person gripping these parts between index finger and thumb and bringing them together in the direction of the central longitudinal axis. The tool can also be applied to the joined distal sections and expand these.

Embodiments of such tools are described in more detail in the co-pending German patent application from the applicant, file number DE 10 2009 014 527.3, which is hereby incorporated by reference.

As has been stated, the section lying in the abdominal wall defines the extent, or lumen, that is then available from the outside for the minimally invasive intervention.

By suitable shaping of the curved transition area between the distal section and proximal section, it is possible to expand this opening slightly further during the pivoting movement, such that a lumen of relatively large diameter is available, which can be considerably larger than a lumen at the distal end of the distal body. This affords the possibility of first making a relatively small skin incision through which the joined distal sections are pushed, and then gently widening the opening during the pivoting movement of the proximal sections towards the longitudinal central axis of the hollow body.

This finally results in an extremely secure and firm fit of the access instrument in the human body, which prevents axial displacement, particularly pulling out, but still permits certain tilting movements.

In an embodiment of the invention, the interacting features are grooves and tongues provided at said edges of said parts.

This measure has the advantage that the groove and tongue structure provides a block against lateral displacement of the joined parts. During pivoting, this groove and tongue structure at the same time guides the rolling movement along the edges when changing between the first position and the second position or vise versa. Due to overlapping of the groove/tongue area, a particular gastight connecting line of the joining proximal sections can be achieved.

In another embodiment of the invention, the interacting features are protrusions and corresponding depressions provided at said edges of said parts.

This measure has the advantage that the joined sections are securely held by structurally simple means that are easy to produce. For example, the external diameter of the protrusions can be made slightly larger than the diameter of the depressions or in a particular shape. The protrusions are pressed correctly into the corresponding depressions or bores, with the result that in this assembled state, for example in the first position, the sections can no longer come apart from each other. With that embodiment, adjoined edges of the parts adhere strongly one to another.

In a combination with the above-mentioned groove and tongue structure, a particular safe assembly, in particular in the transition area between the distal sections and the proximal sections, can be achieved. Additionally, a guiding and a gastight connecting line of the joining edges of the parts can be achieved.

In a further embodiment of the invention, the joined distal sections of the parts result in a rod-shaped distal body having a diameter which is smaller than a diameter of the hollow proximal body.

This measure has the considerable advantage that a distal rod-shaped body of relatively small diameter is initially available for insertion. The actual access created after the pivoting movement is then determined by the structure and the geometry of the joined proximal parts, which can, for example, include the afore-mentioned widening of the access channel into the body. At the same time, the larger diameter of the joined proximal sections affords the possibility of now providing other structural parts in this area, for example valves, connectors or the like. This possibility is also afforded of several instruments now being able to be guided through simultaneously, slightly inclined relative to one another.

In a further embodiment of the invention, the rod-shaped distal body widens from a distal end to a proximal end thereof.

This measure has the additional advantage that an extremely small incision of a few millimeters may be sufficient, onto which the distal end of the rod-like body can be applied. The opening can already be widened slightly as the body, widening from the distal end to the proximal end, is being pushed in. This has proven very useful in interventions performed for example in the navel region.

In a further embodiment of the invention, the joined proximal sections are provided with a cover closing said hollow proximal body against a proximal side.

The provision of a cover has the advantage that the joined proximal sections are closed to the proximal side. This closure can be made by a respective shaping of the proximal ends of the proximal parts or such a cover can be inserted or screwed in.

In a further embodiment of the invention, the cover is designed as a cap fitted to a proximal rim of said hollow proximal body.

Fitting the cap can, for example, ensure the afore-mentioned securing of the two proximal sections that have been joined together or pivoted together. By means of the cap, it is now also possible for the proximal hollow body to be closed off gastight in the proximal direction. Gases for inflating the interior cavity can then be guided through this closed proximal hollow body.

In a further embodiment of the invention, the cap has a seal sealing off said proximal body to said proximal side.

The seal can be provided with several sealed openings, through which sealed openings shaft-like instruments can be passed in a sealed manner.

This seal can be provided with suitable slits or other formations such that, when so desired, instruments can be pushed through the seal, which instruments are then in turn sealed off from the outside by the seal. By suitable configuration of the seal and of the cap, it is then possible, dependent on the intervention, to use different types of seals that permit insertion of several instruments or instruments of different sizes. Hereto, numerous possible variations are afforded.

After the minimally invasive intervention, first the cap is removed and the joined proximal sections are then moved away from the central longitudinal axis, and the distal sections located in the interior of the body are then combined again to form the distal body, which can then be withdrawn from the body via the incision. The parts can also be individually withdrawn from the body.

The cross-sectional geometry of this distal body can be cylindrical, oval, polygonal, triangular or any other, as long as it provides a slim body that can be pushed into the body through an incision. This body can be solid or designed as a hollow body.

Therefore, a particular advantage of this embodiment is that no additional structural elements have to be provided that are spread out from the trocar sleeve, since the trocar sleeve itself is spread open. A further advantage is that no additional mechanism has been built into the hollow body for these procedures, and instead the pivoting of the standing out sections can be effected from the outside.

After withdrawal from the body, the body of the access instrument can be dismantled into the individual parts and easily cleaned and sterilized.

This has hitherto been described on the basis of a body that is assembled from two parts in the shape of half shells, but it will be obvious that this body can also be assembled from three, four or more parts, the basic principle always remaining the same.

In this way, a stable, firmly fitting and immovable access for a minimally invasive intervention is created by structurally and mechanically simple means, and this is achieved using a small number of structural parts that are robust, easy to handle and can also be easily cleaned and sterilized.

In another embodiment of the invention, external thread sections are formed integrally on the outer face of the distal section.

This measure has the advantage that these external thread sections facilitate or assist a screwing-in of the assembled distal body. The introduction of a trocar into the body is a procedure that does not cause bleeding. This is precisely the advantage of minimally invasive surgery. That is to say, the skin is cut only in the surface area, and the rod-shaped body simply has to be driven through the subcutaneous layers, and through a layer of fat possibly lying below, in order to reach the interior cavity. The feature of the thread sections now affords the possibility of this being done not only with a linearly directed movement, but also with a gentle rotation movement, which results in particularly atraumatic insertion into the body.

In another embodiment of the invention, the change-over from the first position to the second position, and vice versa, is effected by pivoting the parts about a transition area between the distal end the proximal section, wherein these joined sections move away from each other, and the sections previously standing outwardly are joined to form a body.

This "synchronous" change-over permits particularly smooth handling of the medical instrument, since the more the proximal sections previously jutting out are moved towards each other, for example, the more the distal sections already inserted in the body are spread apart from each other. There are intermediate positions in which the proximal sections are not yet fully joined together and, accordingly, the distal sections are not yet fully spread apart. In this state, slight corrections can still be made to the fit by the person carrying out this pivoting movement. For example, if the design of the proximal sections is intended to permit an expansion of the opening, it is possible, in such an intermediate position, for the operator to check the exact fit, i.e. whether the sections that are to be spread apart also lie at the correct location. This facilitates handling and leads exactly to a desired fit of the device after the distal sections have been spread apart.

In another embodiment of the invention, the pivoting movement takes place about a pivot axis in the transition area from the distal section to the proximal section, said pivot axis extending perpendicular to the longitudinal central axis.

This pivot axis, which can be a purely virtual pivot axis, facilitates the pivoting movement and contributes to a smooth pivoting movement, which takes place purposefully about the pivot axis.

It is also related to the aforementioned advantage that the pivot axis can also be brought to certain sites which, for example, are required for additional widening. However, the main advantage lies in a reliably guided pivoting movement.

In another embodiment of the invention, the subsidiary bodies are held on each other via swivel joints about whose pivot axis the pivoting movement takes place.

This measure has the advantage that the parts are connected via the swivel joints to form a whole body. The swivel joints themselves then form very clearly defined pivot axes about which the respective proximal and distal sections of a part are pivoted. A construction with two parts, for example, would result in two mutually opposite swivel joints, seen diametrically with respect to the longitudinal central axis, via which swivel joints the two subsidiary bodies are connected and can be pivoted.

In another embodiment of the invention, the parts have, in the area of the pivot axis, complementary hinged-joint features which guide the pivoting movement, without the parts being connected fixedly to each other.

This measure now has the considerable advantage that the hinged-joint features on juxtaposed parts ensure an exactly guided pivoting movement, as is also the case in the aforementioned embodiment with the swivel joints, and at the same time there is the possibility of these two parts being separated from each other after use and being cleaned and sterilized individually. Such hinged-joint features are, for example, a socket-shaped recess in one part, in which a head protruding from the other part can be inserted.

In a further embodiment of the invention, a nose projects from a distal end of said distal section directed away from said longitudinal central axis.

This measure has the advantage that the noses assist the insertion of the parts. An individual part is posed with its nose at the incision, for example in an abdominal wall and the nose, together with the distal section, can be pushed through the incision and through the abdominal wall into the internal cavity. The nose assists to push away the tissue layers with the result that the insertion of a distal section into the body is facilitated by the nose.

In a further embodiment of the invention, an angle α extending between said distal sections spreaded outwardly in said second position amounts to more than 90 degrees.

This measure has the advantage that instruments can be inserted obliquely via the hollow proximal body into the human body and no obstruction occurs by the spreaded distal sections within the human body.

In particular, if several instruments are inserted through the hollow proximal body at the same time, which is a particular advantage of the instrument according to the invention, a wide spreading of the distal section is helpful. This wide spreading supports a main purpose of the invention, this means to have a single port access into the body through which several instruments can be inserted simultaneously.

In a further embodiment, an angle β between an outer longitudinal line of a proximal section and the respective distal section of the same part amounts to more than 90 degrees viewed in a pivoting plane of this part.

This measure has the advantage that when inserting a part into the body via the incision by an operator, there is enough space available to grab the proximal section with a hand.

In combination with the embodiment with the projecting nose has the remarkable advantage that with a part, gripped at the proximal section by hand, can be inserted in a fast and exactly directed movement into the body.

It will be appreciated that the features mentioned above and those still to be discussed below can be used not only in the cited combinations but also in other combinations or singly, without departing from the scope of the present invention.

BRIEF DESCRIPTION OF THE DRAWINGS

The invention is described and explained in greater detail below on the basis of a number of selected illustrative embodiments and with reference to the attached drawings, in which.

DETAILED DESCRIPTION OF PREFERRED EMBODIMENTS

A first illustrative embodiment of a medical instrument shown in FIGS. 1 to 8 is designated overall by reference number 10.

Figure 1:
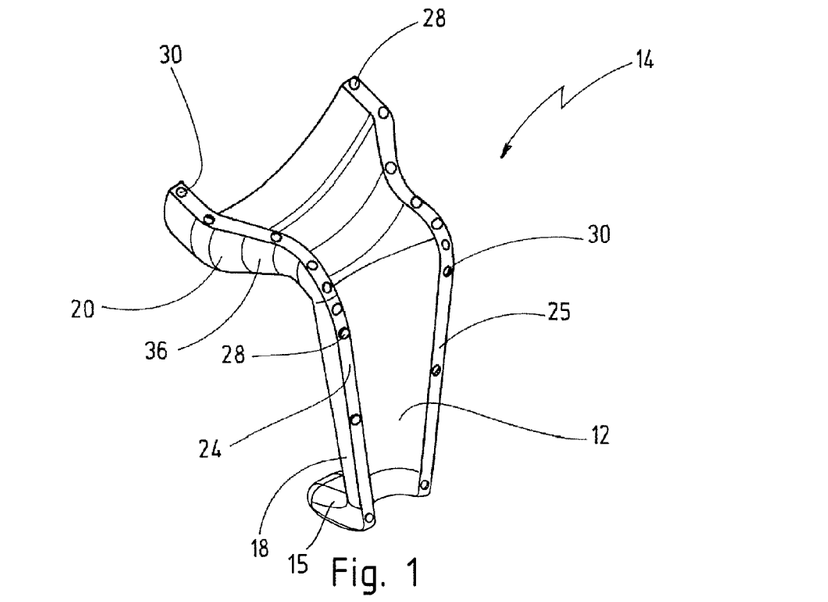
FIG. 1 shows a perspective view of one part of a first embodiment which is composed of two parts in the shape of half shells.

The medical instrument 10 has a body designed as a hollow body 12, of which FIG. 1 shows a part 14, in the shape of a half shell, of this hollow body.

Figure 2:
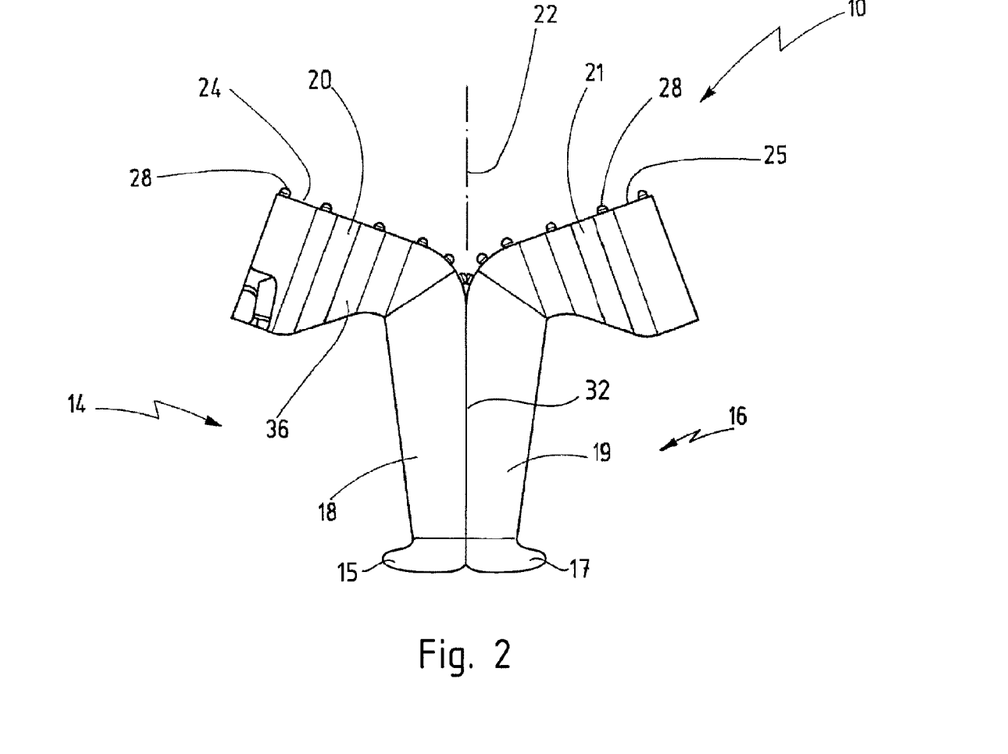
FIG. 2 shows a side view of this embodiment in which two distal sections are joined to form a distal tubular hollow body, and in which the proximal sections stand out to the sides in a Y-shape.

As can be seen from FIG. 2, there is also a second part 16, which has a structure identical to the part 14.

The part 14 has a distal section 18, which corresponds to a half tube that is cut open along the longitudinal axis thereof and that widens from the distal end to the proximal end.

Accordingly, the part 16 has a corresponding distal section 19.

A nose 15 projects laterally from a distal end of the distal section 18. A nose 17 projects similarly from the distal section 19 of the second part 16.

The distal section 18 shown in FIG. 1 is adjoined by a proximal section 20, which is bent out to the side in relation to the distal section 18. The proximal section 20 is also in the form of a half shell. Accordingly, the distal section 19 merges into a corresponding proximal section 21, as can be seen from FIG. 2.

Each of the two parts 14 and 16 has axially extending edges 24 and 25. As can be seen from the perspective view in FIG. 1, protrusions 28 project from the edge 24 in the distal section, whereas depressions 30 are present in the proximal section of this edge 24. On the neighbouring edge 25, this arrangement is exactly the reverse, with depressions 30 present in the distal section of the edge 25, and corresponding protrusions 28 present in the proximal section of the edge 25. As has already been mentioned above, the configuration of the edges on the second part 16 is the same. When, as is shown in FIG. 2, the two identical parts 14 and 16 are assembled, the location of a protrusions 28 on the part 14 is matched by a depression 30 which is present in the corresponding edge of the part 16 and into which such a protrusion 28 can be inserted, and vice versa.

When the two parts 14 and 16 are now placed on each other in such a way that the distal sections 18 and 19 bear on each other via their edges 24 and 25, a body is obtained as shown in FIG. 2. Here, the protrusions 28 that protrude from the edges of one part engage in the corresponding depressions 30 of the other part. As can be seen from FIG. 2, this finally results in a distal hollow body 32, which widens slightly in a conical shape from the distal end to the proximal end.

The proximal sections 20 and 21 are in this case directed or standing away to the sides from the central longitudinal axis 22. The noses 15 and 17 project in the same directions.

This corresponds to the first position of the medical instrument 10.

The individual parts 14 and 16 can be inserted into a human body via an incision 47 in an abdominal wall 48. For example, the part 14 is gripped by a hand at the proximal section 20 and the nose 15 is first posed at the incision 47. The extension of the nose 15 is first directed along the longitudinal central axis 22. After inserting the nose 15 into the incision, the part 14 is brought perpendicular to the abdominal wall 48 and pushed into the internal cavity 49. After inserting the second part 16, the distal sections 18 and 19 are joined via its edges to form the distal body 32 as shown in FIG. 2.

Figure 3:
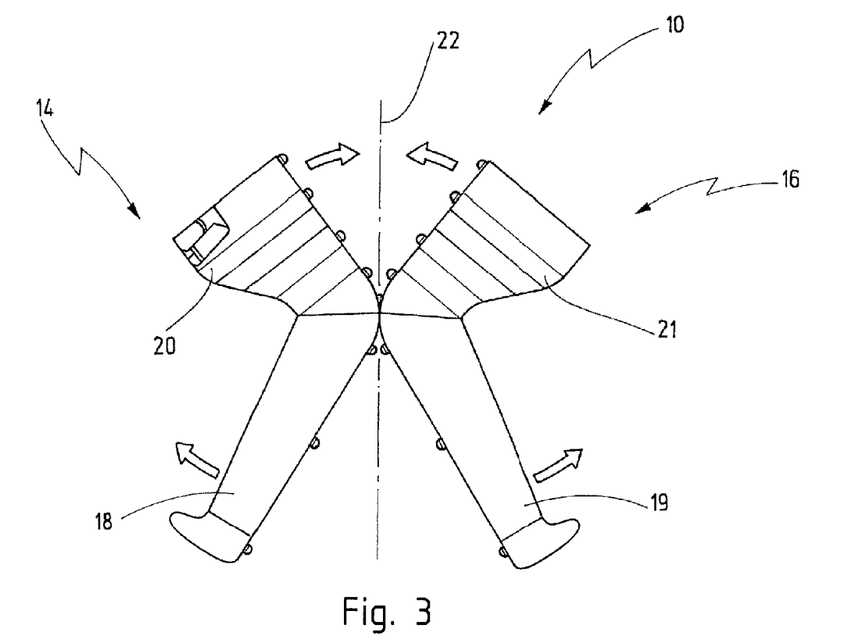
FIG. 3 shows an intermediate position during a pivoting movement of the two parts about or towards each other.
Figure 4:
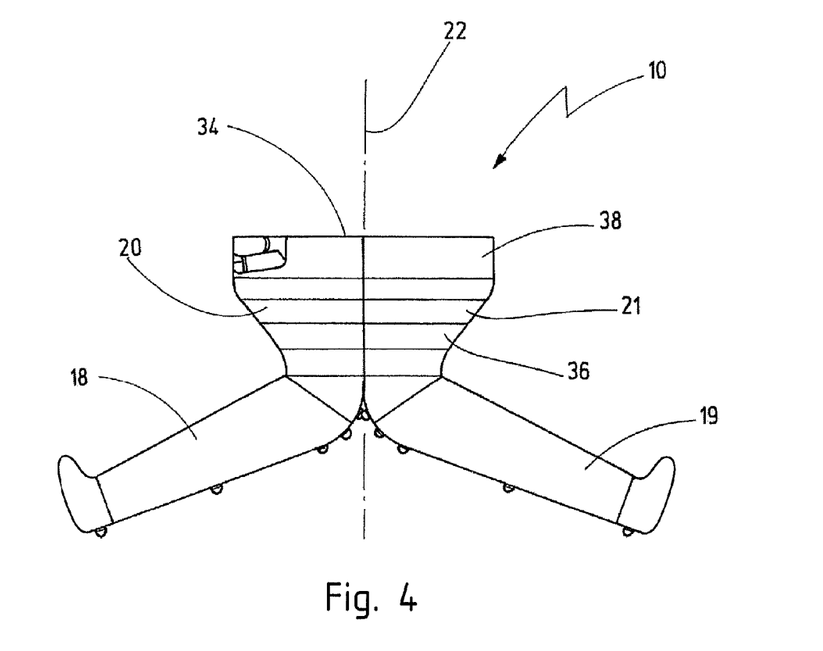
FIG. 4 shows a side view of the two parts in a second position after pivoting from the first position shown in FIG. 2 through the intermediate position shown in FIG. 3.

The assembly as shown in FIG. 2 can now be pivoted or tilted into the second position, shown in FIG. 4, after passing through the intermediate position in FIG. 3.

To do so, as is indicated by arrows in FIG. 3, the two proximal sections 20 and 21 standing out to the sides are moved towards each other in the direction of the central longitudinal axis 22, which can be done manually by an operator, for example by placing the index finger and the thumb on the respective opposite outer edges and pivoting these parts towards each other. At the same time, the distal sections 18 and 19 spread out from the central longitudinal axis 22 during this movement, as is indicated by the arrows in FIG. 3. Special tools can also be used for this purpose, as are described in the aforementioned parallel application.

This pivoting or tilting movement can be carried out until the proximal sections 20 and 21 bear on each other via their edges 24 and 25, thereby forming a proximal hollow body 34.

The transition from the state in FIG. 3 to the state in FIG. 4 occurs very smoothly, since the two parts 14 and 16 roll along each other via their lengthwise edges 24 and 25. The protrusions 28 and the depressions 30 are interacting features blocking a lateral sliding of the parts 14 and 16 transversely to the edges 24 and 25.

It will be seen from the view in FIG. 4 that the proximal sections 20 and 21 merge, via a widened area 36, into an end area 38 that is in the form of an annular flange and that is of considerably greater diameter.

Figure 5:
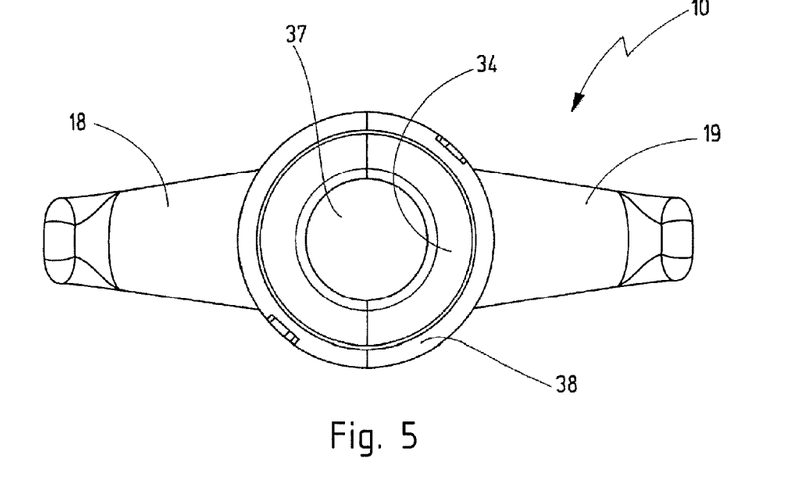
FIG. 5 shows a top view, from the proximal direction, of the assembly in FIG. 4.

This then results in the proximal hollow body 34 which can be seen in FIG. 4 and FIG. 5 and which widens in the proximal direction and is initially open at the top. It will be seen from the plan view in FIG. 5 that an access opening 37 has been created whose diameter is greater than the diameter of the distal end of the assembled distal sections, as can be seen from FIG. 2.

Therefore, this movement also has the effect of expanding or widening the opening or incision 47 that results in the abdominal wall 48 after the distal hollow body 32 has been pushed in.

It will also be seen from the view in FIG. 4 and FIG. 5 that a proximal body 34 is obtained which was widened to a relatively large volume and is assembled from the two proximal sections 20 and 21 in the shape of half shells.

Figure 6:
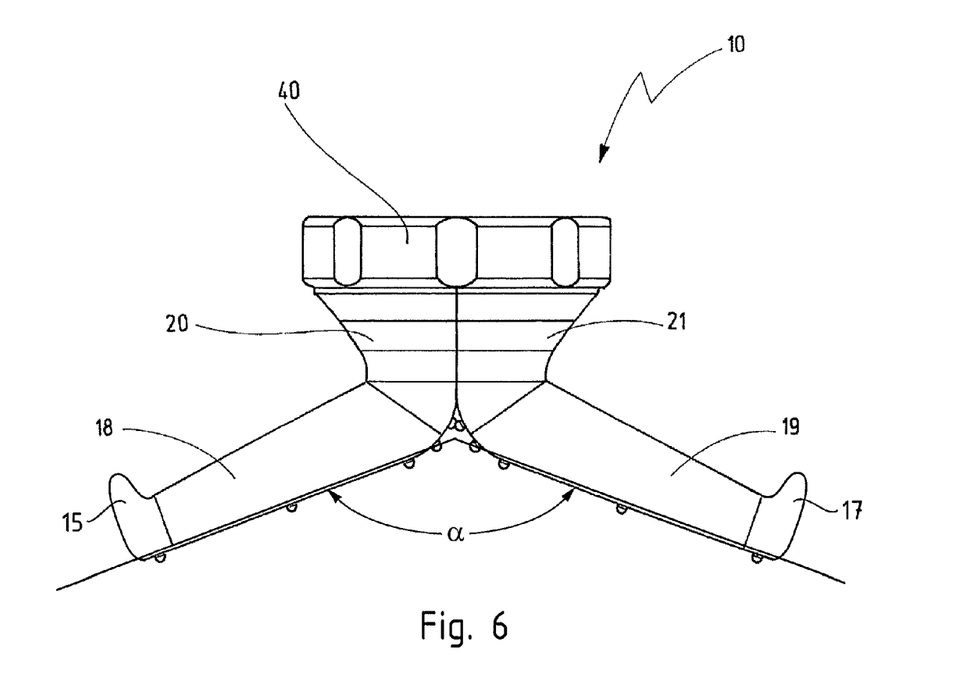
FIG. 6 shows a view corresponding to the side view in FIG. 4, with a cap fitted onto the joined proximal sections.

FIG. 6 shows that a cap 40 is fitted onto the proximal rim of this proximal hollow body 34. It is being possible for said cap 40 to be screwed on, latched on, or applied in the manner of a bayonet catch. FIG. 6 shows an angle $\alpha$ between the spreaded distal sections 18 and 19 as greater than 90 degrees. In that embodiment, the angle $\alpha$ is about 150 degrees. With that spreading angle $\alpha$, shaft-like instruments can be inserted obliquely through the hollow proximal body 34 into the internal cavity 49 without an obstruction by the spreaded distal sections 18 and 19.

Figure 7:
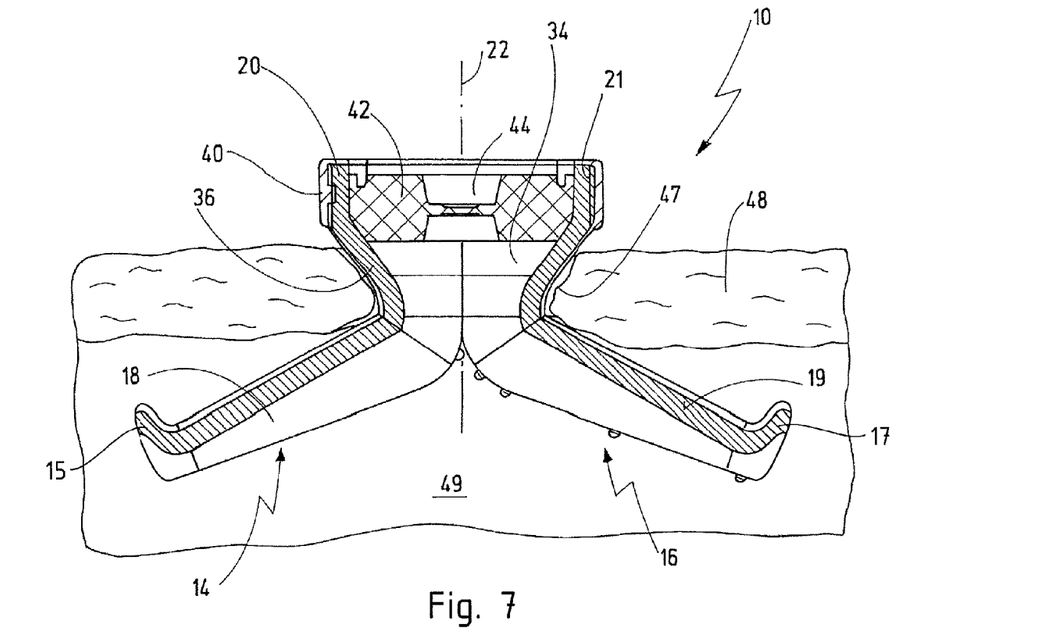
FIG. 7 shows a longitudinal section through the assembly from FIG. 6 and additionally indicates how this assembly is received in an abdominal wall.
Figure 8:
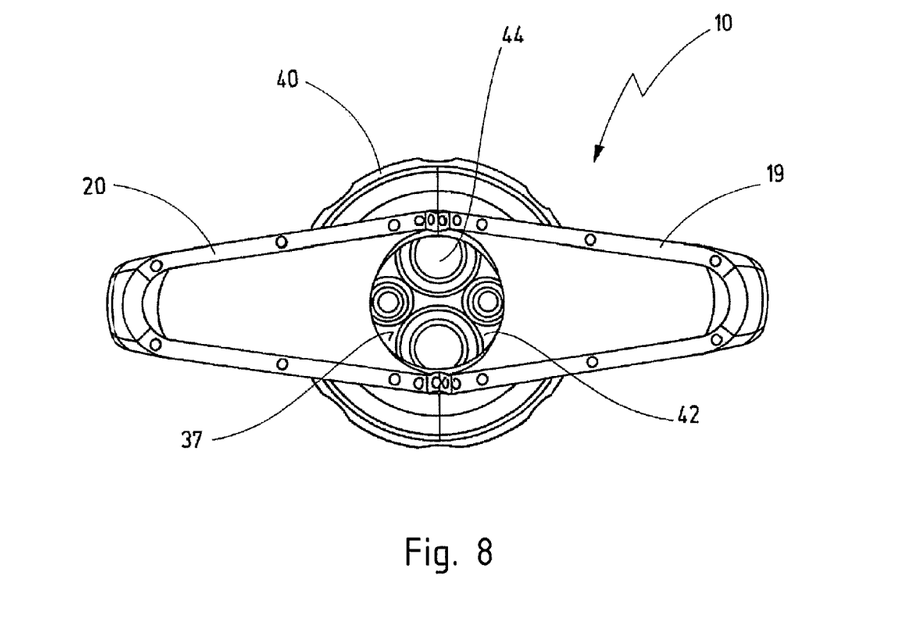
FIG. 8 shows a bottom view, from the distal direction, of the assembly in FIG. 6.

It will be seen from the sectional view in FIG. 7 and from FIG. 8 that a seal 42 is inserted in the cap 40, said seal 42 having at least one opening 44 through which a shaft-like instrument can be pushed sealingly through the medical instrument 10.

FIG. 7 shows how the medical instrument 10 is inserted into the abdominal wall 48 of a human body in order to create an access to the cavity 49 below the abdominal wall 48.

As has already been mentioned above, an incision or small cut was initially made in the skin, said incision corresponding, for example, to the diameter of the distal end of the distal hollow body 32, as is shown in FIG. 2. The noses 15 and 17 then facilitate application to or insertion through this incision.

The medical instrument 10, as shown in FIG. 2, can now be pushed through the abdominal wall, if appropriate with the aid of a trocar mandrel known per se. After the distal sections 18 and 19 have spread open, they bear at least in part on the underside of the abdominal wall 48 and thus ensure a secure fit of the medical instrument 10, secure against excessive tilting and also against being pulled out or pushed in. The spreading angle $\alpha$ of 150 degrees allows not only to have instruments inserted obliquely but also to insert several instruments in differently inclined directions.

The widened area 36 of the proximal sections 20 and 21 limits the depth of insertion of the proximal sections 20 and 21 through the abdominal wall 48 and at the same time also ensures the above-described expansion of the opening 47 in the abdominal wall 48.

It is clear from FIG. 7 that in this state, i.e. in the second position, the medical instrument 10 sits on the abdominal wall 48 in an axially immovable manner and is not at risk of tilting. Suitable surgical interventions can now be performed by way of the medical instrument 10 thus fitted.

After the intervention, the cap 40 is removed and the two proximal sections 20 and 21 are pivoted to the sides away from the central longitudinal axis 22, that is to say run through the sequence from FIG. 4 to FIG. 3 to FIG. 2.

In this state, the medical instrument 10 can be easily withdrawn again from the abdominal wall 48.

Figure 9:
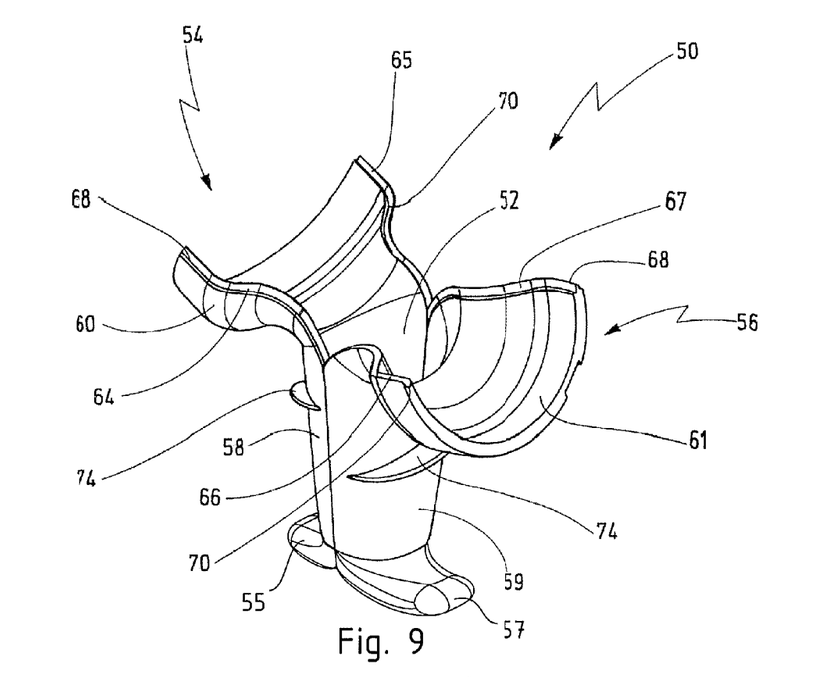
FIG. 9 shows a perspective view of a second illustrative embodiment, this position corresponding to the first position.
Figure 10:
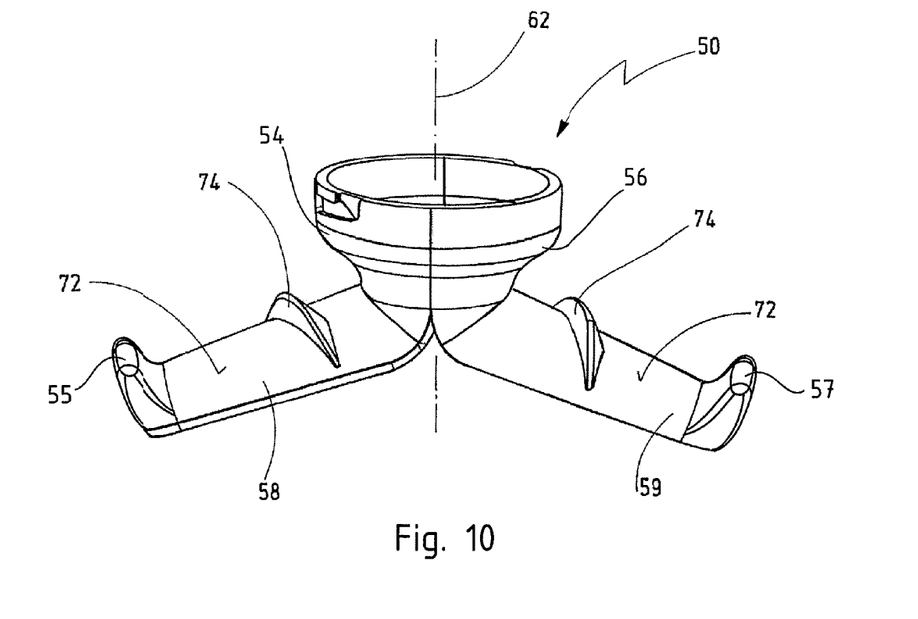
FIG. 10 shows a perspective view corresponding to the view in FIG. 4 and depicting the second illustrative embodiment after pivoting from the first position to the second position.

In the second illustrative embodiment of a medical instrument according to the invention, shown in FIGS. 9 and 10, the medical instrument is designated overall by reference number 50.

The medical instrument 50 is also designed as a hollow body 52 assembled from two identical parts 54 and 56.

Here too, each part 54, 56 again has a distal section 58, 59, and a proximal section 60, 61 standing out to the side. The position shown in FIG. 9 thus corresponds to the first position of the first illustrative embodiment shown in FIG. 2. Noses 55 and 57 project from the distal end of distal sections 58 and 59.

A groove and tongue structure is present along the axially extending edges 64 and 66 of part 54.

The axially extending edge 64 of the part 54 is provided with a tongue 68 in the proximal area thereof. The other edge 65 is provided with a groove 70.

The axially extending edges 66 and 67 of the other part 56 have the same design. Both parts 54 and 56 are designed identically.

As can be seen from FIG. 9, a groove 70 of the part 54 faces a tongue 68 of the opposite part 56. The same is valid for the other edges. The groove and tongue structure can extend into the distal sections 58 and 50.

This groove and tongue structure not only ensures that the two parts 54 and 56, joined together as in FIG. 9, do not come loose from each other, but also that the tongue and groove structure provides a guiding action during the pivoting movement from the first position, as shown in FIG. 9, to the second position, as shown in FIG. 10. As can be seen from FIG. 10, the second position once again results in a body of the kind that has been described above, for example with reference to FIG. 4. The groove and tongue structure allows a gastight joining of the proximal sections 54 and 56 along its adjacent edges.

External thread sections 74 arranged on the outer faces 72 of the distal sections 58 and 59 facilitate and guide the insertion of the medical instrument 50, in the position shown in FIG. 9, through an opening in an abdominal wall in the form of a rotation movement. The same then applies when the joined distal sections 58 and 59 are turned out from the body after an intervention. Here too, hollow bodies 52 are present which are again symmetrical with respect to the central longitudinal axis 62 and which are in this case also assembled from two parts 54 and 56.

A cap can again be fitted in this case too.

In a third illustrative embodiment of a medical instrument, shown in FIGS. 11 to 14, the medical instrument is designated overall by reference number 80.

It will be seen from FIGS. 11 to 14 that in this case too a hollow body 82 is again present which is assembled from two identical parts 84 and 86 in the shape of half shells. Here too, distal sections 88 and 89 are again present which can be suitably assembled in the manner described above, as shown in FIG. 11, and the proximal sections 90 and 91 are pivoted or jut out to the sides from the central longitudinal axis 99, in this case approximately at right angles. In other words, the spreading angle of the distal section 88 and 89 is 180 degrees, as can be seen from FIG. 13.

Figure 11:
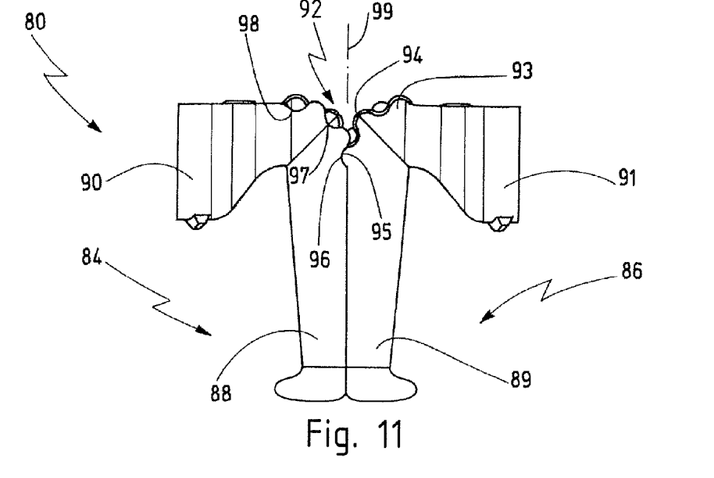
FIG. 11 shows a view comparable to FIG. 2 and depicting a third illustrative embodiment whose edges have hinged-joint features.
Figure 12:
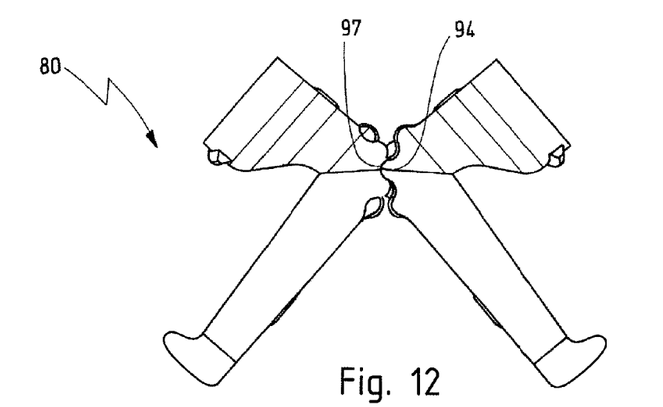
FIG. 12 shows an intermediate position comparable to the view in FIG. 3.
Figure 13:
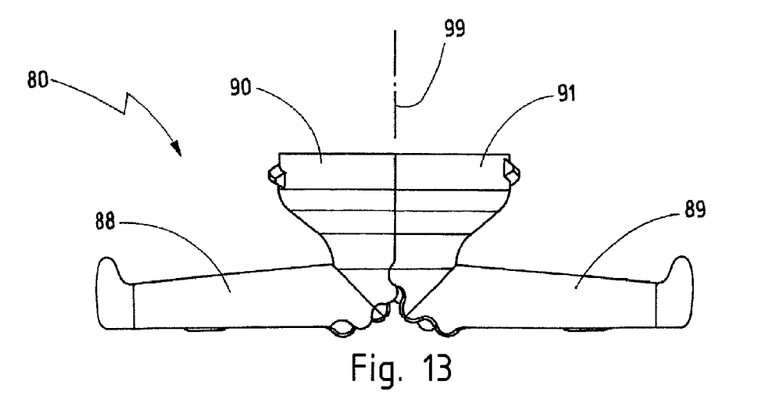
FIG. 13 shows a view comparable to FIG. 4 and depicting the second position of this illustrative embodiment.
Figure 14:
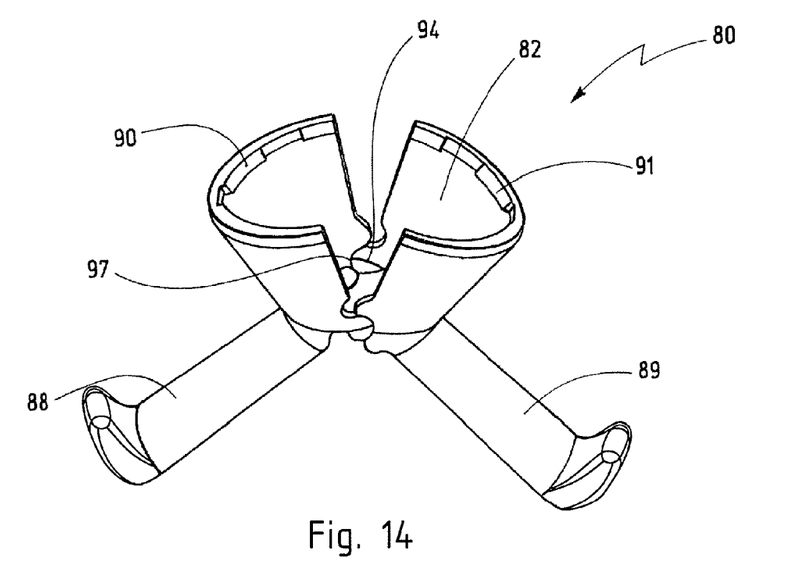
FIG. 14 shows a partially simplified perspective view of the intermediate position from FIG. 12.

In this case too, as is shown by the sequence running from FIG. 11 to FIG. 12 to FIG. 13, this assembly can be pivoted such that the proximal sections 90 and 91 form a proximal hollow body.

Hinge joints 92 are arranged in the transition area from the respective distal section to the respective proximal section.

As is depicted on the right-hand side of FIG. 11, three disc-like joint heads 93, 94 and 95 are provided on the lengthwise edge of the part 86 directed towards the observer and can engage in corresponding complementary joint sockets 96, 97 and 98 in the part 84.

Corresponding joint heads (not shown in detail here) are also present on the edge of the part 84 directed towards the observer and engage in joint sockets, on the part 86, which are present between the joint heads 93, 94 and 95 thereof. Complementary arrangements are accordingly present on the respective rear edges, only the other way round. Parts 84 and 86 are designed identically.

It will be seen from the change-over from FIG. 11 to FIG. 13, and also in particular from the intermediate position in FIG. 12, that these hinge joints 92 allow the subsidiary bodies 84 and 86 to roll smoothly along each other during the pivoting movement. The method of use is the same as in the illustrative embodiments described above, and it is also once again possible for a cap to be fitted here. It will be seen from FIG. 13 that the distal sections 88 and 89 are here pivoted through approximately 90 degrees, such that they bear on the underside of an abdominal wall across a long and extensive surface area and thereby ensure a particularly secure hold. A cap (not shown) can be fitted to the proximal end of joined proximal sections 90 and 91.

Figure 15:
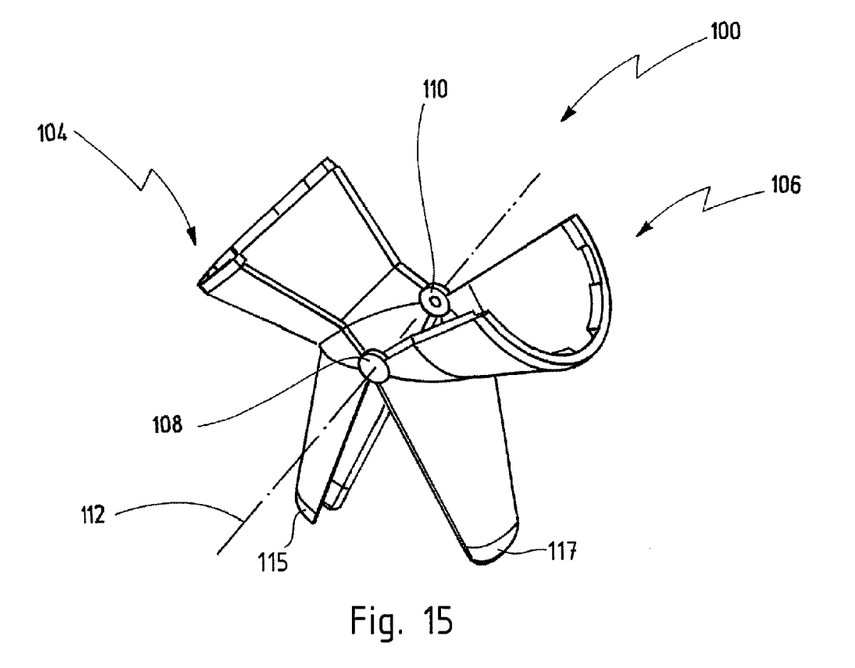
FIG. 15 shows a view corresponding to the perspective view in FIG. 14 and depicting a fourth illustrative embodiment with a fixed joint axis.

In the fourth illustrative embodiment of a medical instrument, shown in FIG. 15, the medical instrument is designated overall by reference number 100.

The medical instrument 100 is assembled from two parts 104 and 106, which are connected to each other via fixed swivel joints 108 and 110. There is therefore a defined pivot axis 112 about which the two parts 104 and 106 can pivot to and fro between the first position and the second position in the above-described pivoting movements. Otherwise, the two subsidiary bodies 104 and 106 are basically designed in the same way as the bodies described above. The distal ends of the distal section are provided with bevels 115 and 117 for facilitating the insertion of the distal body through an incision.

The fixed swivel joints 108 and 110 can be designed such that they can still be easily released, so as to permit better cleaning and sterilization of the two subsidiary bodies 104 and 106 then released from each other.

Figure 16:
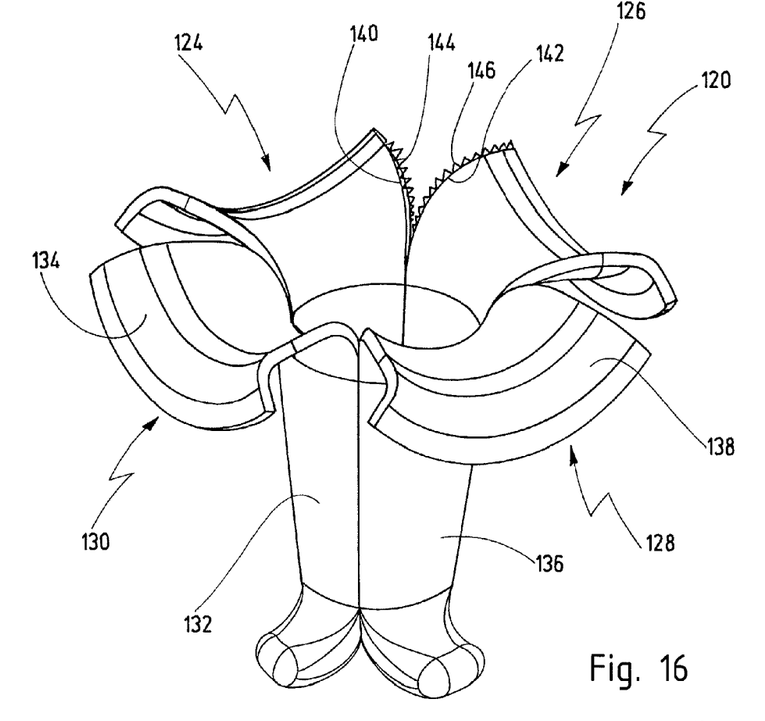
FIG. 16 shows a perspective view of a fifth illustrative embodiment assembled from four parts, specifically seen in the first position.
Figure 17:
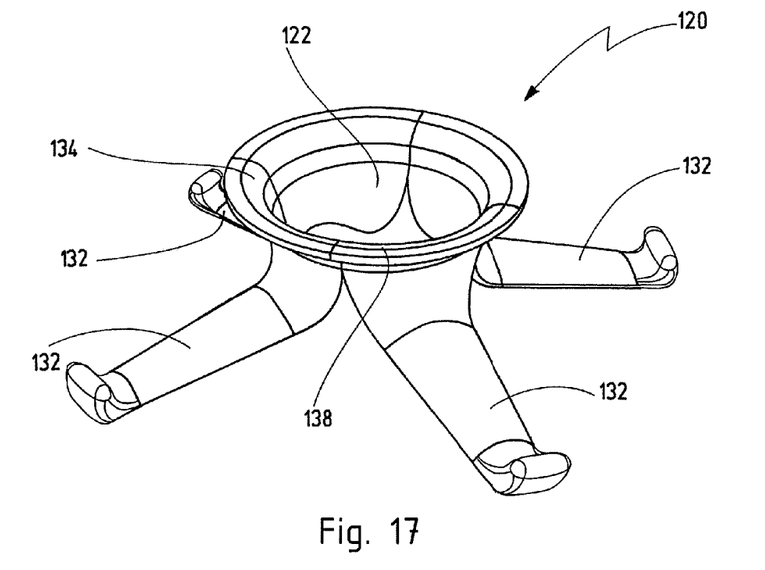
FIG. 17 shows a perspective view of the embodiment from FIG. 16 in the second position, with the distal sections spread out to the sides.

In the fifth illustrative embodiment of a medical instrument according to the invention, shown in FIGS. 16 and 17, the medical instrument is designated overall by reference number 120.

The medical instrument 120 is also designed as a hollow body 122, which is here assembled from four parts 124, 126, 128 and 130.

Each one of these parts once again has a corresponding distal section 132 and, angled out from the latter, a proximal section 134, this arrangement being depicted here only for the part 130, for the sake of clarity. In principle, this medical instrument 120 is also once again of the same structure, the only difference being that there are four parts which, in the first position as shown in FIG. 16, can be joined such that a distal hollow body 136 is obtained which, as has been described above several times, can then be pushed into a body through an incision. Noses at the distal ends of the distal sections 132 facilitate the insertion of the four parts 124-130 as individual parts.

Here too, the four distal sections each bear on corresponding adjacent sections via their two edges.

For the change-over from the first position, shown in FIG. 16, to the second position, shown in FIG. 17, the pivoting movement described above is again carried out, thereby resulting in the body in FIG. 17, which has a proximal hollow body 138 from which the four expanded distal sections 132 jut out.

As can be seen from FIG. 16, complementary toothed arrangements 144 and 146 are present on the edges, here the edges 140, 142 of two adjoining sections 124 and 126, and guide the rolling movement of the subsidiary bodies during the pivoting from the position in FIG. 16 to the position in FIG. 17. Here too, a corresponding cap can be fitted in place in the position shown in FIG. 17.

If the toothed arrangement is made as a spiral gearing, this again avoids a lateral sliding transversely to the edges.

FIGS. 18 through 23 show a sixth illustrative embodiment of a medical instrument, which is designated overall by reference number 150.

Figure 18:
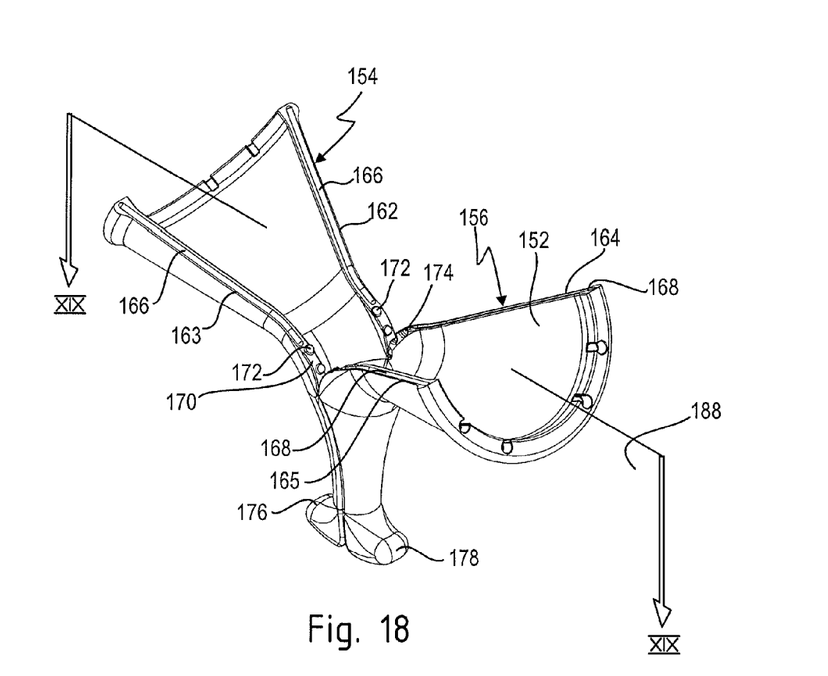
FIG. 18 shows a perspective view of a sixth illustrative embodiment with the distal sections joined together.
Figure 19:
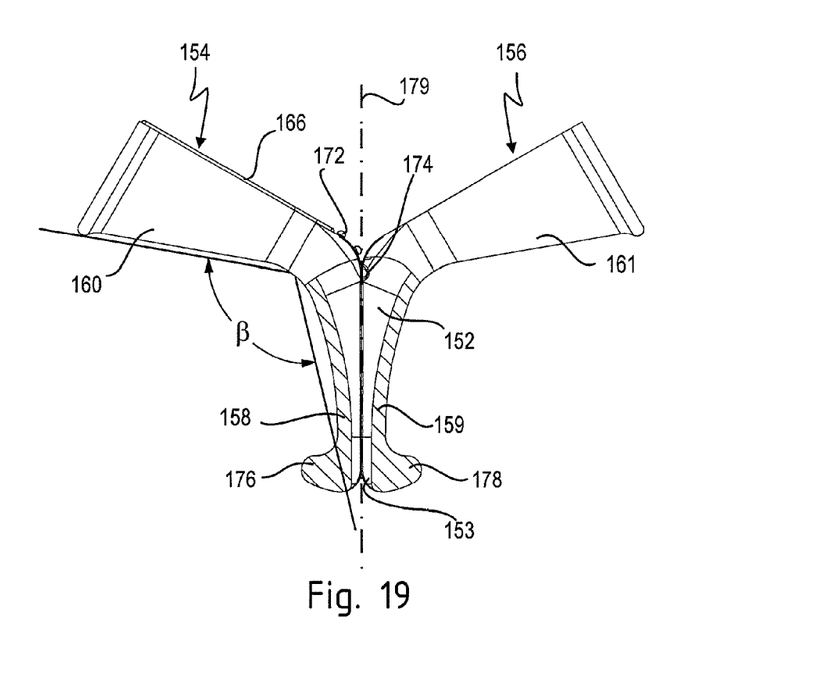
FIG. 19 shows a longitudinal section of the joined distal sections along the XIX-XIX in FIG. 18.
Figure 20:
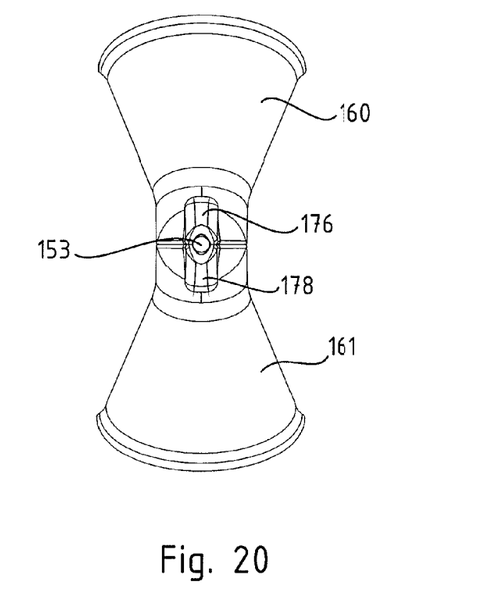
FIG. 20 shows a bottom view, from the distal direction of the assembly of FIG. 18.

From FIGS. 18 to 20 it can be seen that the medical instrument 150 is designed as a hollow body 152.

The hollow body 152 is again assembled of two opposing parts 154 and 156.

Each of the two parts 154 and 156 has a distal section 158 and 159 and a proximal section 160 and 161 which is standing laterally outwards from the distal section 158 and 159.

Within that embodiment, edges 162 and 163 of the part 154 are provided with a tongue 166. The edges 164, 165 of the part 156 are provided with grooves 168.

This means that the two parts 154, 156 are designed differently. If the two parts 154 and 156 are assembled along its edges, tongues 166 of part 154 faces grooves 168 of the part 156.

Figure 21:
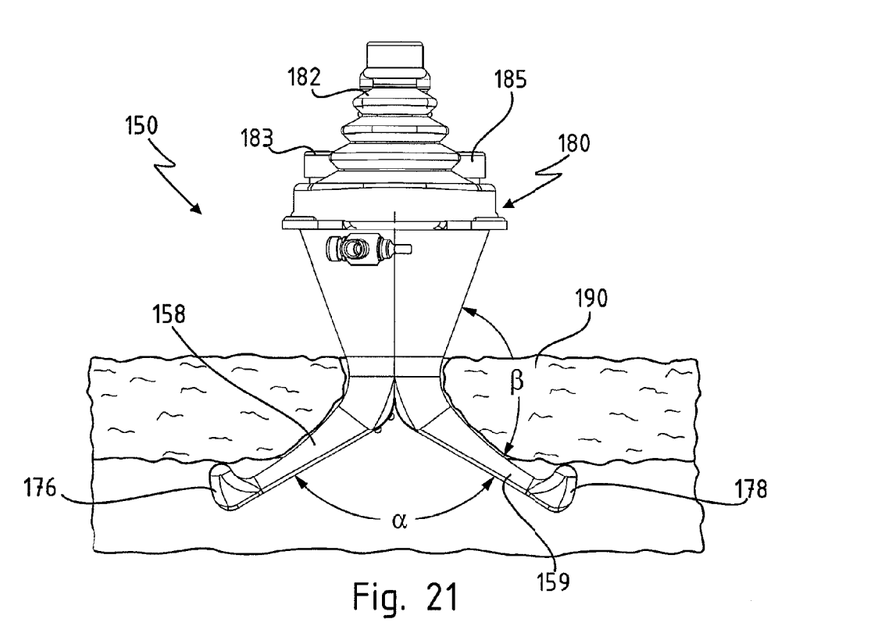
FIG. 21 shows a side view of the sixth embodiment with spreaded distal sections, a cap fixed to the proximal end of the proximal body and inserted into an abdominal wall.
Figure 22:
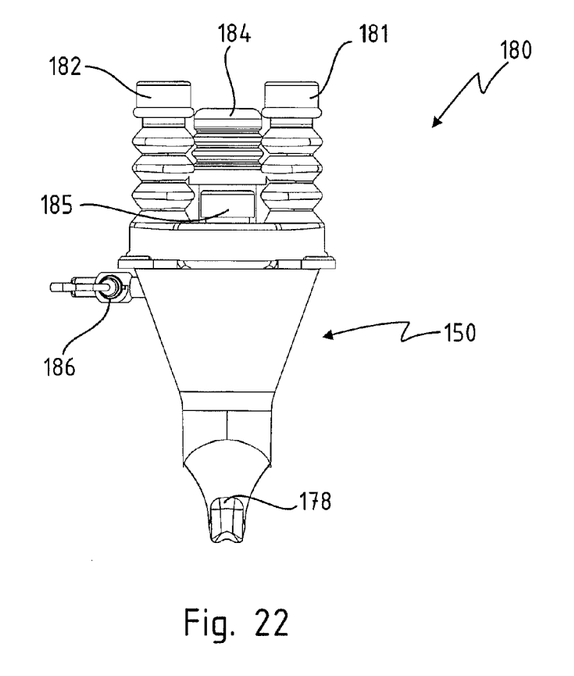
FIG. 22 shows a further side view turned about 90 degrees about the longitudinal central axis compared to FIG. 21.
Figure 23:
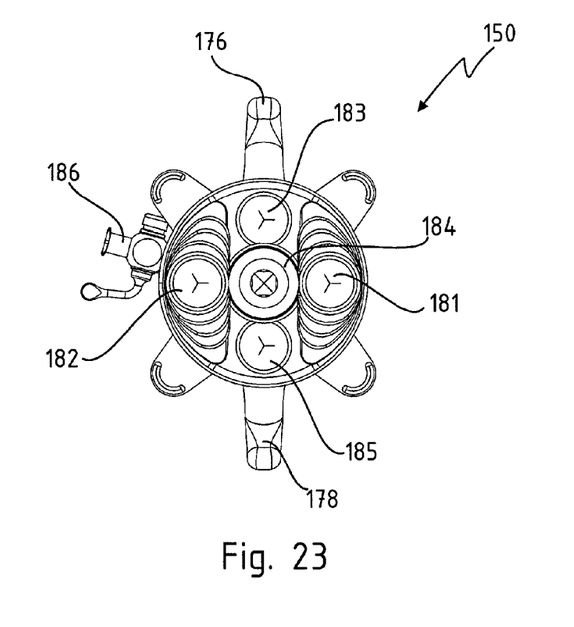
FIG. 23 shows a top view from the proximal direction of the sixth embodiment.

With that, a laterally sliding of the joined parts is avoided. Additionally, the material and the design of groove and tongue is such that a gastight closure is provided between the edges of the proximal sections 160 and 161 if they are assembled as shown in FIGS. 21 through 23.

In a transition area 170 between the distal and the proximal sections, protrusions 172 are provided at part 154, which can engage in opposing depressions 174 at the other part 156.

The protrusions 172 and the depressions 174 lead to an exact guiding of the two parts 154 and 156 during pivoting it between its first and second positions. Additionally, they avoid a laterally sliding and provide additional tightening features in said transition area 170.

A nose 176 and 178 projects laterally from the distal end of parts 158 and 159.

The noses 176, 178 project approximately rectangular from a longitudinal central axis 179 of the distal hollow body 152. The noses 176, 178 extend in the same direction as the sections 160 and 161, as can be seen from FIG. 19.

From this view, it can also be seen that the two adjacent joined distal sections 158, 159 surround a throughhole 153. With that throughhole 153 it is possible to already insert a shaft-like viewing instrument, for example an endoscope, through the assembled parts 154 and 156.

As can be seen from FIGS. 21 through 23, a cover shaped as a cap 180 is fitted on a distal rim of the joined proximal sections 160 and 161. The cap 180 can be made of an elastic material and therefore, the cap tights itself. If the cap 180 is made of a stiff material, an additional seal is provided.

From FIGS. 21 through 22 it can be seen that two opposing bellow domes 181, 182 stand up from the cap 180. Between the bellow domes 181, 182, three seal openings 183, 184 and 185 are provided.

The outer distal ends of these seals are designed as self-closing slit seals. If no shaft-like instrument is inserted through said seals, they seal against the outside.

A laterally mounted LUER connection 186 allows to insert a gas through the medical instrument 150 into the body, for example for inflating the body to facilitate an inspection of the inner cavity. In particular, in that case it is important that the cap 180 and the different seals also seal with shaft-like instruments inserted through the seals. A seal along the joining lines of the proximal sections 160, 161 is assured due to the above-mentioned groove and tongue structure. The LUER connection 186 can be provided at a proximal section 160 or 161 of parts 154 or 156. The LUER connection can also be provided at the cap 180.

The spreading angle α of the spreaded distal sections 158 and 159 is about 125 degrees. The projecting noses 176, 178 abut at the underside of the abdominal wall 190 and act as an additional measure against tilting of the device.

As can be seen from the top view of FIG. 23, five shaft-like instruments can be inserted through the different seal openings 181-185. Due to the dome-like shape of the bellow domes 181, 182, instruments inserted through those seals can be tilted extremely, since the bellow dome structure can follow these tilting movements.

As a result, through one medical instrument 150 according to the invention, which can be inserted into a body via a single incision, several shaft-like instruments can be inserted. This instrument can be tilted extremely, therefore, manipulations in a broad range can be made within the cavity via one single access opening.

This is regarded as a particular advantage of this construction as a "SINGLE PORT ACCESS".

From FIGS. 19 and 20 it can be seen that an angle β between an outer line of the proximal section 160 and the respective distal section 158 is greater than 90 degrees. This angle β lies in a sweeping plane 188 which corresponds to the section plane along lines XIX-XIX in FIG. 18.

With such angles β greater than 90 degrees, an operator can grip a proximal section 160 or 161 of a part 184 or 186 via hand and can locate the respective nose at an incision, whereby this handling is not obstructed by the abdominal wall 190. Therefore, an individual part 154 or 156 can be easily and quickly inserted. These two parts can be joined together facilitated by the groove and tongue structure within the human body resulting to the structure as shown in FIGS. 18 and 19.

For pivoting the medical instrument from the first position into the second position, the proximal sections 160, 161 can be gripped by hand. Due to the groove and tongue structure in connection with the protrusions and depressions, this pivoting can be made exactly directed into the second position as shown in FIGS. 21 through 24. The protrusions 172 and the depressions 174 support this rolling movement in the transition area 170.

After fitting a cap 180, the medical instrument 150 is ready for working. If no sufficient view is available within the cavity, a gas can be supplied through the LUER connection 186 for inflating the inner cavity. Subsequently up to five shaft-like instruments can be inserted through the different seals within the cap 180 for performing a minimally invasive intervention. If one shaft-like instrument is withdrawn, the seal opening closes gastight. After the intervention, the cap 180 is removed and the two parts 154, 156 can be withdrawn assembled or as individual parts.

The invention claimed is:

1. A minimally invasive access instrument for creating an access for a minimally invasive intervention, comprising:

a body having a longitudinal central axis, said body being assembled of at least two parts, each of said parts having edges extending along a direction of said axis, and said parts being assembled via said edges, each of said parts having a distal section merging into a proximal section standing outwardly from said longitudinal central axis when said distal section extends in said axis, wherein in a first position said distal end sections of said parts are joined along said edges to form a distal body with said proximal sections standing outwardly, and in a second position, said proximal sections of said parts are joined along said edges to form a hollow proximal body with said distal sections standing outwardly, wherein a change-over from said first position to said second position, and vice versa, can be brought by pivoting said parts along a curved transition area between said distal sections and said proximal sections of said edges without a separate holding element holding said parts together, and wherein said edges being provided with interacting features which are designed to block a lateral sliding of said joined parts transversely to said edges, said interacting features comprising projections projecting from one edge and engaging with respective recesses in an opposite edge, each of said respective recesses having side walls that prevent said lateral sliding of a projection once said projection is in engagement with said recess, said interacting features at said edges providing a guide guiding said pivoting along said curved transition area and preventing a lateral slipping away of said edges and providing a gastight seal along said proximal sections of said edges in said second position.

2. The instrument of claim 1, wherein said interacting features are grooves and tongues provided at said edges of said parts.

3. The instrument of claim 1, wherein said interacting features are protrusions and corresponding depressions provided at said edges of said parts.

4. The instrument of claim 1, wherein said joined distal sections of said parts result in a rod-shaped distal body having a diameter which is smaller than a diameter of said hollow proximal body.

5. The instrument of claim 4, wherein said rod-shaped distal body widens from a distal end to a proximal end thereof.

6. The instrument of claim 1, wherein said joined proximal sections are provided with a cover closing said hollow proximal body against a proximal side.

7. The instrument of claim 6, wherein said cover is designed as a cap fitted to a proximal rim of said hollow proximal body.

8. The instrument of claim 7, wherein said cap has a seal sealing off said proximal hollow body to said proximal side.

9. The instrument of claim 8, wherein said cap is provided with several sealed openings, through which sealed openings shaft-like instruments can be passed in a sealed manner.

10. The instrument of claim 1, wherein an outer face of said distal sections of said parts is provided with external thread sections.

11. The instrument of claim 10, wherein said pivoting takes place about a pivot axis in said curved transition area, said pivot axis of said parts extending perpendicular to said longitudinal central axis.

12. The instrument of claim 1, wherein a nose projects from a distal end of said distal section directed away from said longitudinal central axis.

13. The instrument of claim 1, wherein an angle $\alpha$ extending between said distal sections standing outwardly in said second position amounts to more than 90 degrees.

14. The instrument of claim 1, wherein an angle $\beta$ extending between an outer longitudinal line of a proximal section and a respective distal section of a same part amounts to more than 90 degrees viewed in a pivoting plane of said parts.

* * * * *